United States Patent [19]

Hochstrasser et al.

[11] Patent Number: 5,292,665
[45] Date of Patent: Mar. 8, 1994

[54] CATALYST FOR PREPARING POLYACRYLAMIDE GEL WHICH IMPROVES THE DETECTION OF BIOMATERIALS BY SILVER STAINING

[75] Inventors: Denis F. Hochstrasser, Geneva, Switzerland; Carl R. Merril, Rockville, Md.

[73] Assignee: The United States of America as represented by the Department of Health and Human Services, Washington, D.C.

[21] Appl. No.: 849,344

[22] Filed: Mar. 11, 1992

Related U.S. Application Data

[63] Continuation of Ser. No. 323,851, Mar. 15, 1989, abandoned.

[51] Int. Cl.$^5$ ............................................. G01N 21/77
[52] U.S. Cl. ..................................... 436/86; 436/174; 436/905; 204/180.1; 204/182.8
[58] Field of Search ................ 436/86, 79, 174, 905; 204/180.1, 182.6, 182.8; 524/521, 728; 525/279

[56] References Cited

U.S. PATENT DOCUMENTS

| | | | |
|---|---|---|---|
| 4,189,370 | 2/1980 | Boschetti | 204/299 |
| 4,421,915 | 12/1983 | Ponticello et al. | 544/387 |
| 4,555,490 | 11/1985 | Merril | 436/86 |
| 4,654,132 | 3/1987 | Takagi et al. | 204/182.8 |
| 4,874,490 | 10/1989 | Hochstrasser | 204/182.1 |
| 4,912,011 | 3/1990 | Yamamoto et al. | 430/138 |
| 4,950,708 | 8/1990 | Hochstrasser | 524/728 |

OTHER PUBLICATIONS

Artoni et al., Fractionation Techniques in a Hydro—Organic Environment Analytical Biochemistry 137, 1984, pp. 420–428.
Aldrich, p. 620, catalog No. D17,930-2.
Kirk—Othmer, Encyclopedia of Chemical Technology, 3rd Edition, vol. 22, 1983, pp. 978–982.
Hochstrasser et al., Development of Polyacrylamide Gels . . . Staining, Analytical Chemistry 173, 412–423 (1988).
U.S. Dept. of Commerce, NTIS publication PB88-179809 May 17, 1988.
U.S. Dept. of Commerce, NTIS publication PB88-212758 Apr. 7, 1988.

*Primary Examiner*—James C. Housel
*Assistant Examiner*—Long V. Le
*Attorney, Agent, or Firm*—Leydig, Voit & Mayer

[57] ABSTRACT

A polyacrylamide gel comprising acrylamide and diacrylylpiperazine. A method for providing a polyacrylamide gel comprising employing a catalyst system which comprises dimethylpiperazine, sodium thiosulfate or a mixture thereof and ammonium or potassium persulfate. The use of the gel as the matrix in a silver staining procedure for the detection of biomaterials, provides for the obtainment of reduced background staining.

15 Claims, 1 Drawing Sheet

CATALYST FOR PREPARING POLYACRYLAMIDE GEL WHICH IMPROVES THE DETECTION OF BIOMATERIALS BY SILVER STAINING

This is a continuation of application Ser. No. 07/323,851, filed Mar. 15, 1989, now abandoned.

BACKGROUND OF THE INVENTION

1. Field of the Invention

The present invention relates to a novel polyacrylamide gel and process for the preparation thereof. The polyacrylamide gel improves silver stain methods for detecting biomaterials, such as proteins, polypeptides, nucleic acids, and the like, which had been separated by electrophoresis procedures. Particularly, the novel polyacrylamide gel provides for the detection of proteins by ammoniacal silver staining with reduced background staining.

2. Discussion of Related Art

In the past, various methods have been used for protein analysis. Such methods include the Kjehdahl method, a colorimetric method, and others. In more recent times, electrophoresis techniques were employed. For example, a protein sample was fixed onto a matrix, such as a polyacrylamide gel, and subjected to electrophoretic separation. This separation is accomplished by exposing the sample to an electric field which causes the various components of the sample to migrate at different rates within the matrix. These different rates are dependent on the charge of the individual components, as well as on the other physical and chemical properties thereof. Following the migration, a certain migration pattern is formed. Various methods for defining such migration patterns have developed, such as visual determination methods. Radioautography and staining are among the procedures which are included within the visualization methods.

Radioautography is conducted, for example, with intrinsically labelled proteins produced from substrates containing radioactive labelled amino acids. See article by P. H. O'Farrell, in J. Biol. Chem., Vol. 250, pp. 4007–4021 (1975). Moreover, extrinsic radioactive labelling techniques, such as iodination, can alter the electrophoresis properties of proteins, and the isotope is not necessarily uniformly linked to each protein and non-selectively distributed among all polypeptide components of the mixture.

Direct iodination of separated proteins in polyacrylamide gels has been reported by Edler et al. (see the article by J. H. Edler, R. A. Peckett, II, J. Hampton, and R. A. Lerner in the J. Biol Chem., Vol. 252, pp. 6510–6515 (1977)). This technique is quite useful when used to study radioactive peptides after tryptic digestion, but it has been found that some lots of acrylamide contain a contaminant which also becomes radioiodinated, and this negates its utility for radioautography.

Even though radioautography is a powerful visualization tool, it has certain disadvantages. For example, it is slow and complex. Also, it involves modifications to the proteins prior to electrophoresis.

One of the methods known for visualization of protein is described in U.S. Pat. No. 4,405,720. The stain described in this patent requires the use of three solutions and it takes a minimum of about 30 minutes to perform. Furthermore, the technique described in said patent does not stain proteins or nucleic acids in thin membranes such as cellulose nitrate.

Coomassie blue stain, the most commonly employed protein stain, takes hours to perform and it lacks the sensitivity to detect proteins present in low concentrations in biological fluids or tissues. Sensitivities achieved with heavy metal stains or fluorescent stains, on the other hand, were found to be less than, or at best, equivalent to Coomassie blue (about 10 ng of protein). Merril et al., *Electrophoresis*, 1982, pp. 327–342. Recently, more than a hundred-fold increase in sensitivity over that obtained with Coomassie staining was achieved by adapting a histological silver tissue stain for use with polyacrylamide gels. de Olmos, *Brain, Behav. Evol.* 2, 313–237 (1969), Switzer, et al. *Anal. Biochem.* 98, 231–237 (1979), Merril, et al. *Proc. Natl. Acad Sci. U.S.A.* 76, 4335–4339 (1979). This stain could detect as little as a tenth of a nanogram of protein and an image could be achieved in less than 6 hours.

There are a number of known methods useful in staining proteins which utilize silver. For example, L. Kerenyi, et al., Clin. Chim. Acta 38, 465–467 (1972), describes a method for demonstrating proteins in electrophoretic, immunoelectrophoretic and immunodiffusion preparations, whereby the preparations are treated with potassium ferrocyanide, which is transformed during development into silver ferrocyanide and then into colloidal silver grains. The physical developer contains anhydrous sodium carbonate, ammonium nitrate, silver nitrate, tungstosilicic acid and formalin, and the protein in the preparations stain dark brown with a page gray background.

R. C. Switzer, et al., *Anal. Biochem.* 98, 231–237 (1979), and C. R. Merril, et al., Proc. Natl. Acad. Sci. U.S.A., 76 No. 9, 4335–4339 (1979), describe a silver stain technique for detecting proteins and peptides in polyacrylamide gels which is a modification of de Olmos' neural, cupric-silver stain. The procedure consists of ten steps and utilizes an aqueous solution of silver nitrate and cupric nitrate and involves treatment with a diamine solution, which is known to sometimes form an explosive silver amide complex. The proteins stain as dark spots on a darkened background.

B. A. Oakley, et al., Anal. Biochem. 105, 361–363 (1980), simplified the above procedure of Switzer, et al., by reducing the number of steps involved to six and also reducing the amount of silver required without diminishing the sensitivity of the technique. However, the manner in which the proteins stain was not changed, i.e., dark stain on a darkened background.

A further modification of the Switzer, et al., procedure was made by R. C. Allen, Electrophoresis I, 32–37 (1980), who increased the sodium to ammonium ion ratio, which resulted in increased silver deposition.

C. R. Merrill, et al., Anal. Biochem, 110, 201–207 (1981), modified and simplified the above procedure of Kerenyi, et al., adapting it to acrylamide gels.

D. Goldman, et al., Clin. Chem. 26 No. 9, 1317–1322 (1980), report that when using a procedure essentially the same as that of Merrill, et al. (PNAS, 1976), and Switzer et al., (Anal. Biochem., 1979), proteins from samples of cerebral spinal fluid stained in shades of yellow, red and blue.

C. R. Merrill, et al., Science 211, 1437–1438 (1981), describe a silver stain procedure for proteins separated by two-dimensional gel electrophoresis, which requires treatment with potassium dichromate and nitric acid prior to staining with silver nitrate followed by washing and then immersion in an image developer containing formalin and sodium carbonate. There is no indication of color development with this stain procedure.

Poehling and Neuhoff, Electrophoresis 1981, 2, 141-147, describe a silver stain suitable for acrylamide gels of 0.5 to 1 mm thickness which requires a pretreatment with glutardialdehyde under controlled temperatures prior to staining with a diamine solution.

Marshall and Latner, Electrophoresis 1981, 2, 228-235, describe a silver stain method which requires a treatment with paraformaldehyde and sodium cacodylate prior to staining with a modified diamine solution wherein methylamine is substituted for ammonium hydroxide. Ochs et al., Electrophoresis 1981, 2, 304-307, and Sammons and Adams, Electrophoresis 1981, 2, 135-145, describe a silver stain procedure of which the present invention is a modification.

With the exception of the 1980 Goldman et al. procedure and the method of Sammons and Adams, all of the silver stain techniques described above only stain proteins in varying shades of brown or black.

U.S. Pat. No. 4,416,998 describes a silver stain procedure, wherein a substance capable of binding silver is treated with a glutaraldehyde solution, an aqueous silver salt solution, a reducing solution and an aqueous carbonate or sulfate solution. The procedure also enables one to stain a variety of substances, including protein, in varying shades of color.

U.S. Pat. No. 4,582,808 describes a silver staining method comprising pretreating a carrier, such as a polyacrylamide gel, with an alcoholic solution containing polyethylene glycol or polyoxyethylene alkylphenol, followed by treating the pretreated carrier with a solution of silver nitrate. This method is disclosed as having a shortened operation time and an improvement in the reproducibility of staining.

U.S. Pat. No. 4,555,490 describes a method using light ("photodevelopment") to develop a metallic silver image of biopolymers, particularly nucleic acids and proteins separated on polyacrylamide gels, whereby it is possible to visualize protein and nucleic acid patterns within 10 minutes after electrophoretic separation. This "photodevelopment" method requires only two solutions: a solution to "fix" the proteins and a solution containing silver ions, which produces an image when exposed to light. This type of protein stain has achieved a sensitivity of about 0.5 ng of protein. DNA separated on polyacrylamide may also be visualized with this stain.

U.S. Pat. No. 4,575,452 describes a method and kit for the optical detection of proteins and nucleic acids in a matrix, such as polyacrylamide electrophoresis gels. The method comprises fixing the proteins and nucleic acids in the matrix using aromatic sulfonic acids having tertiary amines capable of forming coordination complexes with silver ion.

U.S. Pat. No. 4,672,043 describes a method for determining macromolecules in polyacrylamide gels comprising the steps of forming a latent stain image by nucleating the macromolecules in the gel with a palladium tetramine salt and developing the latent stain image by treating the gel with a physical developing solution comprising dimethylamine borane and a transition metal salt. The improvement comprises contacting the developed latent stain image with a 1-phenyl-2-tetrazoline-5-thione or a salt of 1-phenyl-1H-tetrazole-5-thiol.

U.S. Pat. No. 4,690,901 describes a staining technique for specimens, which involves the sequential treatment of specimens with periodic or hydrochloric acid, thiocarbohydrazide or thiosemicarbazide, and silver methenamine. The technique, when using periodic acid, provides an excellent stain to evaluate glycomacromolecules and fibrovascular tissue and to conduct a broad spectrum of staining procedures for all modes of microscopy. Use of hydrochloric acid facilitates evaluation of cell nuclear DNA and chromatin.

U.S. Pat. No 4,695,548 describes gel inserts comprising a solidified liquid, such as agarose, suitable for use in an electrophoretic method, lysed cells entrapped within a matrix formed by the solidified liquid and macromolecules, such as DNA or intact chromosomes derived from the lysed cells, may be advantageously used in electrophoretic separations. The gel inserts are placed directly in a suitable support medium and subjected to one or more electric fields to separate the macromolecules.

U.S. Pat. No. 4,468,466 describes a silver stain method for protein in gels utilizing treatment with a reducing agent followed by treatment with a silver salt and actuating irradiation, the improvement comprising the use of a reducing agent consisting essentially of dithiothreitol in an amount effective to stain the protein but keep background staining to a minimum.

As illustrated above, silver staining methods, which employ polyacrylamide gel for detecting biomaterials, are widely used. However, unacceptable background staining drawbacks are associated with each of these illustrative methods, including the method of U.S. Pat. No. 4,468,466, which is mentioned as keeping background staining to a minimum.

Recent observations concerning the mechanisms of silver stains have led to the development of a polyacrylamide gel, which does produce very little, if any, background staining. The key observations, which permitted the development of this gel, are: the essential nature of basic amino acids containing sulfur in the detection of peptides by the silver staining reaction; and evidence that the active groups in the basic amino acids, the imidazole, guanidine and amino groups, or the sulfur groups in the sulfur containing amino acids, require cooperative effects. That is, they function poorly when they are isolated in a polymer, but if two or more basic amino acids of sulfur containing amino acids are in close proximity, then a good staining reaction will occur. These studies on the mechanisms of silver stains led the present inventors to determine that the amide groups in methylene-bisacrylamide crosslinking agent might be responsible at least partially for the background found with the silver stains. Methylene-bisacrylamide contains two amide groups, which are separated by a single carbon. In this study, the present inventors have demonstrated the role of these amide groups in the formation of the background stain by studying the silver stain reaction in gels containing varying ratios of acrylamide to the methylene-bisacrylamide crosslinking agent. By utilizing different crosslinking agents, the present inventors have demonstrated that the appearance of background staining depends mainly on the presence of and the position of the amido groups in the crosslinking agents. It depends also on the presence of other groups in the crosslinker or the acrylamide chain.

SUMMARY OF THE INVENTION

An object of the present invention is to provide a novel polyacrylamide gel.

Another object of the present invention is to provide a method for producing the polyacrylamide gel.

A further object of the present invention is to provide an ammoniacal silver staining biomaterial detection method with reduced background staining.

The present invention relates to a polyacryl amide gel comprising acrylamide and diacrylylpiperazine. Preferably, the weight ratio of acrylamide to diacrylylpiperazine (PIP) is about 15 to 0.4.

The present invention further relates to a method for preparing a polyacrylamide gel comprising polymerizing acrylamide with diacrylylpiperazine in the presence of a catalyst system which comprises dimethylpiperazine or preferably sodium thiosulfate and ammonium persulfate or potassium persulfate. More preferably, the catalyst system comprises a mixture of dimethylpiperazine, sodium thiosulfate and ammonium persulfate or potassium persulfate.

Yet further, the present invention relates a silver stain method for the detection of biomaterials with reduced background staining, the improvement which comprises the use of a polyacrylamide gel comprising acrylamide and diacrylylpiperazine as the matrix. Preferably, the silver stain method is an ammoniacal silver stain method and the biomaterials are proteins.

In a more preferred silver stain method for the detection of biomaterials with reduced background staining, the improvement comprises the use of a polyacrylamide gel produced by polymerizing acrylamide with diacrylylpiperazine as the matrix in the presence of a catalyst system, which comprises dimethylpiperazine, sodium thiosulfate or a mixture thereof and ammonium persulfate or potassium persulfate.

Figure 1:
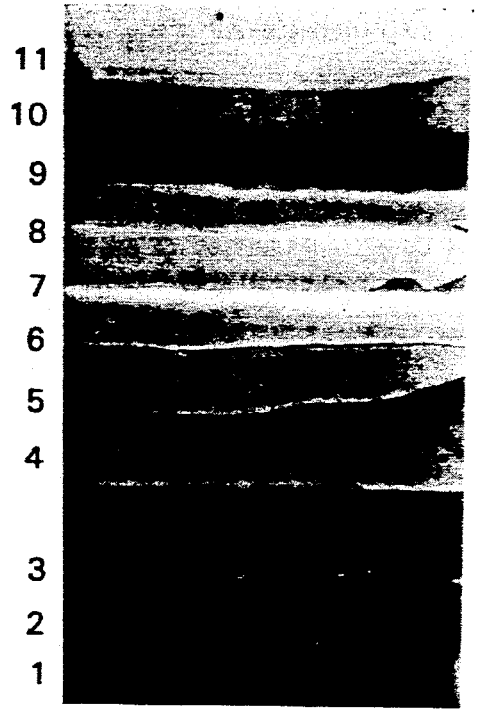
FIG. 1 is a photograph of an electrophorasis gel, which illustrates the effects of different diamine catalysts on silver staining in polyacrylamide gels. A volume of 150 µL of ammonium persulfate solution was used in all gel bands, except for the band containing 1,4-diazabicyclo(2,2,2)octane which required 800 µL of ammonium persulfate solution for an identical polymerization rate. The varying amounts of diamines, were chosen to obtain similar rate of polymerization. It was impossible to produce a gel with equivalent mechanical properties with triethylamine, 1,3-diaminopropane or 1,5-diazabicyclo(4,3,0)non-5ene. The polymerization was much poorer with these three reagents. All the bands were polymerized with diacrylylpiperazine (PIP) as the crosslinking agent except band one which was polymerized with methylenebisacrylamide (BIS) and TEMED to illustrate the current commonly employed gel polymerization system.

APS: 1 g/L
KPS: 0.67 g/L
All other salt solutions: 0.75 g/L
TEMED (N,N,N'N'-tetramethylethylenediamine): 3.3 mL/L
DMPIP (1,4-dimethylpiperazine): 20 mL/L
BIS: methylene-bisacrylamide 0.8 g/100 mL stock solution
PIP: diacrylyl-piperazine 0.1 g/100 mL stock solution θ: no diamine used; the concentration of persulate was increased.

This gel demonstrated that the lowest background staining could be achieved by polymerizing at a polyacrylamide gel with diacrylylpiperazine (PIP) as crosslinking agent, with dimethylpiperazine and ammonium or potassium persulfate as the catalytic system. Background staining was further minimized if the catalytic system contained sodium thiosulfate.

Despite extensive washing procedures and/or preelectrophoresis of the gel, the background staining was profoundly affected by the diamine, the salts and the oxido-reducing catalyst. This observation provides indirect evidence that these compounds may be incorporated in the structure of the gel. Small ions should have been removed by preelectrophoresis and washing procedures. The diamine bases and anions are probably incorporated into the gel matrix. The lack of an effect with the cations suggest that they are not incorporated into the gel under the basic conditions utilized in these experiments.

DETAILED DESCRIPTION OF THE INVENTION

The above objects and advantages in accordance with the present invention are achieved by providing a novel polyacrylamide gel. The polyacrylamide gel is comprised of acrylamide and diacrylylpiperazine. Preferably, the weight ratio of the acrylamide to diacrylylpiperazine comprised in the polyacrylamide gel is about 30 to 0.8. The novel polyacrylamide gel is formed by a method comprising polymerizing acrylamide with the crosslinker, diacrylylpiperazine, in the presence of a catalyst system which comprises dimethylpiperazine or preferably sodium thiosulfate and ammonium or potassium persulfate. More preferably, the catalyst system, comprises a mixture of dimethylpiperazine, sodium thiosulfate and ammonium persulfate or potassium persulfate. Preferably, the catalyst system is present in an amount of about 0.8 to 16 mg/g based on the total weight of the acrylamide and diacrylylpiperazine. In further accordance with the foregoing, the employment of the novel polyacrylamide gel as the matrix in an ammoniacal silver staining procedure for the detection of biomaterials, particularly proteins, provides for the obtainment of reduced background staining.

The formation of background staining has limited the sensitivity, reproducibility, and quantitative analyses, of most polyacrylamide gel silver staining methods. It was found that methylenebisacrylamide (BIS), the most commonly used gel crosslinker, was partially responsible for this background stain, when polyacrylamide gels were stained with ammoniacal silver nitrate. Gels polymerized with BIS appear black and opaque after a prolonged development time. The development of a new crosslinking agent, diacrylyl-piperazine (PIP) profoundly diminished this background staining with ammoniacal silver stain. However, after a prolonged development period, a yellow background still appeared. The residual yellow background which was obtained with the PIP crosslinked gels, appeared to be related to the catalyst used for the polymerization of the gel.

Many catalyst systems have been suggested in the past. The most commonly used contain: ammonium persulfate (APS) or potassium persulfate (KPS), riboflavin (RFN) and N,N,N'N'-tetramethylethylenediamine (TEMED). The catalytic systems can be divided in two general groups: a) one in which free radicals are generated by photocatalysis and another b) in which free radicals are generated by oxydo-reduction reactions.

a) The agent most widely used as photo-catalyst, RFN, was suggested for vinyl group polymerization four decades ago. Its photo-decomposition can be enhanced by cinnamyl alcohol or by the dye methylene blue-triethanolamine. The use of riboflavin-5'-phosphate (RFP) has also been proposed. The photodecomposition of these riboflavin molecules produces the free radicals.

Riboflavin molecules have several disadvantages: they cannot be used at acidic polymerization conditions (pH 3), when the catalyst system has to be optimized for the gel and buffer system considered; they require highly reproducible UV or visible light illumination to get reproducible gels especially in a casting chamber when multiple gels are polymerized Uranyl nitrate can be used as a photopolymerizing agent at a low pH, but the hazards associated with its uses (radioactivity, possible explosive material obtained), although small, are cumbersome.

b) The redox systems most commonly used are APS or KPS and a diamine compound as an adjunct catalyst. TEMED is the most commonly used diamine and occasionally, dimethylaminopropionitrile (DMPN) is utilized. It has been suggested to replace the diamine with sodium sulfite or even silver nitrate. The redox system most rarely used is hydrogen peroxide-ferrous sulfate ascorbic acid, also called Fenton's reagent. Difficulties in controlling the rate of polymerization have been reported for this system. The acetic acid, which was often used in the staining procedure, may also react with the hydrogen peroxide to form peracetic acid, which has a tendency to attack the Plexiglas electrophoretic apparatuses.

None of the systems outlined above has been found to be optimal for the polymerization of gels, when silver stain techniques are used to detect proteins. Photocatalytic agents have been avoided because of the difficulties in obtaining reproducible polymerization in gel casting chambers.

The diamine-persulfate system produces a yellow background stain with ammoniacal silver after a prolonged development period.

The current study presents the results of a number of diamine-salt catalytic systems on the polymerization and the silver staining of gels. A new catalytic system, which further delays or even prevents the appearance of a background stain with ammoniacal silver stain and which, therefore, enhances protein detection, is described.

Chemical structures of diamines used:

| | | |
|---|---|---|
| 1. | $NH_2-CH_2-CH_2-CH_2-NH_2$ | 1,3-diaminopropane |
| 2. | $CH_3-N(CH_3)-CH_2-CH_2-CH_2-NH$ | 3-dimethylaminopropylamine |
| 3. | $CH_3-N(CH_3)-CH_2-CH_2-C\equiv N$ | dimethylaminopropionitrile |
| 4. | piperidine-$N-CH_2-CH_2-C\equiv N$ | 1-piperidinepropionitrile |
| 5. | morpholine-$N-CH_2-CH_2-N(CH_3)-CH_3$ | dimethylaminoethylmorpholine |
| 6. | $CH_3-N(CH_3)-CH_2-CH_2-NH_2$ | dimethylethylenediamine |
| 7. | $CH_3-N(CH_3)-CH_2-CH_2-NH-CH_2-CH_3$ | dimethylethylethylenediamine |
| 8. | $CH_3-N(CH_3)-CH_2-CH_2-N(CH_3)-CH_3$ | N,N,N'N'-tetramethylethylenediamine (TEMED) |
| 9. | $CH_3-N$(piperazine)$N-CH_3$ | dimethylpiperazine (DMPIP) |
| 10. | diazabicyclo ring | diazabicyclo(2,2,2)octane |

MATERIALS AND METHODS

Apparatus

The model 175 chamber (Bio-Rad, Richmond, Calif.) was employed for isoelectric focusing (IEF) separation. Sodium dodecylsulfate (SDS) polyacrylamide gel electrophoresis (PAGE) separation was performed in the Protean II ® chamber (Bio-Rad, Richmond, Calif.). Power was supplied with a 3000/300xi power supply (Bio-Rad, Richmond, Calif.) for IEF separation, and 700 V 1.6 Amp HP power supply (Hewlett-Packard, Palo Alto, Calif.) for the SDS-PAGE separation. The gels (180×200×1.5 mm) were cast either in the Protean II ® casting chamber or on the stand-alone casting device (Bio-Rad, Richmond, Va.).

Reagents

The following reagents were used: acrylamide, N,N'-methylene-bisarylamide, N,N,N'N'-tetramethyle-thylenediamine (TEMED), ammonium persulfate, triethylamine, 1,3-diaminopropane, 3-dimethyl-aminopropylamine, 1-piperidinepropionitrile, dimethyl-ethylenediamine, dimethylethylethylenediamine, 1,4-dimethylpiperazine, piperazine, 4(2(dimethylamino)ethyl)morpholine, 1,5-diazabicyclo(4.3.0)non-5ene, 1,4-diazabicyclo-(2.2.2)octane, Tris HCl, citric acid, cholamidopropyldimethylhydroxypropanesulfonate (CHAPS), ampholytes 3.5–10 and 5–7 (source: LKB, Broma, Sweden); potassium persulfate, sodium sulfate, sodium sulfite, sodium hydrosulfite, sodium bisulfite, potassium metabisulfite, sodium thiosulfate, sodium permanganate and magnesium sulfate.

Procedure—Effects of Varying the Diamine Compounds

Acrylamide stock solutions are prepared by dissolving acrylamide and either N,N'-methylenebisacrylamide or diacrylylpiperazine in water in the following amounts: stock solution M contained 30 g of acrylamide and 0.8 g of methylene-bisacrylamide, stock solution P contained 30 g of acrylamide and 1.0 g of diacrylylpiperazine. These stock solutions are each adjusted with deionized water to a final volume of 100 ml. Tris HCl stock solution T (1.5M, pH 8.8) is prepared by dissolving 181 g of Tris HCl in 1 L of deionized water and adjusting the pH to 8.8 with concentrated HCl.

A stock solution A is prepared for the polymerization of the gels by mixing 16.5 mL of deionized water with 14.6 mL of Tris HCl stock solution T and 24 mL of acrylamide/BIS stock solution M. A stock solution B is prepared for the polymerization of the gels by mixing 16.5 mL of deionized water with 14.6 mL of Tris HCl solution T and with 24 mL of acrylamide/PIP stock solution P.

Solution 1 contains 5 mL of solution A and 20 $\mu$L of TEMED; solution 2 contains 5 mL of solution B and 150 $\mu$L of diaminopropane; solution 3 contains 5 mL of solution B and 100 $\mu$L of dimethyl-aminopropylamine; solution 4 contains 5 mL of solution B and 50 $\mu$L of piperidinepropionitrile; solution 5 contains 5 mL of solution B and 10 $\mu$L of dimethylethylenediamine; solution 6 contains 5 mL of solution B and 10 $\mu$L of dimethylethylethylenediamine; solution 7 contains 5 mL of solution B and 10 $\mu$L of TEMED; solution 8 contains 5 mL of solution B and 60 $\mu$L of dimethylpiperazine; solution 9 contains 5 mL of solution B and 400 $\mu$L of dimethylaminoethylmorpholine; solution 10 contains 5 mL of solution B and 800 $\mu$L of 100 g/L diazabicyclooctane solution.

Polymerization is initiated sequentially by the addition of 150 $\mu$l of ammonium persulfate stock solution (10 g/100 ml of water) to each of the ten gel solutions. In the actual procedure, the polyacrylamide gels are prepared by first preparing the following solution: 173 mL of Tris HCl solution (pH 8.8, 1.5M), 265 mL of acrylamide/diacrylylpiperazine solution (30 g/0.8 g in a final volume of 100 mL with deionized water) and 207.5 mL of deionized water. Prior to degassing the solution, 4 mL of thiosulfate solution (5 gm of 100 mL in deionized water) is added; then 4 mL of dimethylpiperazine and 5 mL of ammonium persulfate solution (10 gm in 100 mL of deionized water) are added to initiate the polymerization and form the gels. Each of the gels is cast by gently pouring 2 ml of each of the solutions in sequential order between two glass plates separated by 1.5 mm spacers, at 4 min. intervals. The stepwise composite gel, a "zebra" gel is removed from between the glass plates 2 hr. later and stained as described in "Protein detection" discussed below.

Studies with gels polymerized with different oxydo-reducing agents and adjunct compounds The same stock solutions A and B described above are used. Stock solution S is prepared by dissolving 10 g of ammonium persulfate in 100 mL of deionized water. Stock solution K is prepared by dissolving 30 g of potassium persulfate in 100 mL of deionized water. All the other salt solutions (sodium sulfate, permanganate, bisulfite, etc.) are prepared by dissolving 5 g of the considered salt in 100 mL of deionized water. The gel is cast by gently pouring 2 ml of each of the solutions described below immediately after their preparation between two glass plates separated by 1.5 mm spacers.

Solution 11 contains 2.5 mL of solution A, 10 $\mu$L of TEMED and 30 $\mu$L of solution S; solution 12 contains 2.5 mL of solution B, 10 $\mu$L of TEMED and 30 $\mu$L of solution S; solution 13 contains 2.5 mL of solution B, 10 $\mu$L of TEMED and 60 $\mu$L of solution K; solution 14 contains 2.5 mL of solution B, 60 $\mu$L of dimethylpiperazine (DMPIP) and 60 $\mu$L of solution K; solution 15 contains 2.5 mL of solution B, 60 $\mu$L of DMPIP and 30 $\mu$L of solution S; solution 16 contains 2.5 mL of solution B, 10 $\mu$L of TEMED, 50 $\mu$L of sodium sulfate solution and 100 $\mu$L of solution K; solution 17 contains 2.5 mL of solution B, 10 $\mu$L of TEMED, 50 $\mu$L of sodium permanganate solution and 100 $\mu$L of solution K; solution 18 contains 2.5 mL of solution B, 10 $\mu$L of TEMED, 50 $\mu$L of sodium bisulfite solution and 100 $\mu$L of solution K; solution 19 contains 2.5 mL of solution B, 10 $\mu$L of TEMED, 50 $\mu$L of sodium hydrosulfite solution and 100 $\mu$L of solution K; solution 20 contains 2.5 mL of solution B, 10 $\mu$L of TEMED, 50 $\mu$L of potassium metabisulfite and 100 $\mu$L of solution K; solution 21 contains 2.5 mL of solution B, 10 $\mu$L of TEMED, 50 $\mu$L of magnesium sulfate and 100 $\mu$L of solution K; solution 22 contains 2.5 mL of solution B, 10 $\mu$L of TEMED, 50 $\mu$L of sodium thiosulfate solution and 100 $\mu$L of solution K; solution 23 contains 2.5 mL of solution B, 10 $\mu$L of TEMED and 50 $\mu$L of solution K; solution 24 contains 2.5 mL of solution B, 600 $\mu$L of solution K, but no TEMED or DMPIP.

High Resolution Potential of Gels (2-DGE) Polymerized with the New Catalyst System.

Two-dimensional gel electrophoresis (2-DGE) offers the greatest electrophoretic resolution currently available. Catalyst systems are tested for their resolving power in a high resolution 2-DGE system. The isoelectric focusing (IEF) and SDS-PAGE gels are prepared according to publication, Hochstrasser, D.F., Harrington, M., Hochstrasser, A.C., Miller, M.J., Merril, C.R. (1988), Anal. Biochem. vol. 173, p. 214-232, except for the second dimension separation, where TEMED is replaced by DMPIP (6x the TEMED volume) and sodium thiosulfate is added in the same proportion as in the previous paragraph. Sample preparation, sample loading and running conditions are according to said publication.

Protein detection

Silver stain detection of proteins is performed following the procedures of publications, Hochstrasser, D.F., Harrington, M., Hochstrasser, A.C., Miller, M.J., Merril, C.R. (1988), Anal. Biochem. vol. 173, p. 214-232, and Oakley, B. R., Kirsch, D.R., Morris, N.R. (1980), Anal. Biochem. 105, 361-363: After the separation of proteins is completed, the gels are washed in water for 5 min., in ethanol: acetic acid: water (40:10:50) for 1 hour, and then in ethanol:acetic acid:water (5:5:90) for ≥3 h. or overnight. After a water wash of 5 min., the gels are then soaked for 30 min. in a 10% glutaraldehyde solution. The glutaraldehyde is removed by extensive water washes, 3×10 min. washes followed by 4×30 min. washes. The ammoniacal silver nitrate solution is prepared by the slow addition of a solution containing 6 g of silver nitrate in 30 ml of deionized water to a solution containing 10 ml of ammonium hydroxide 25%, 1.5 ml of 10N sodium hydroxide and 160 ml of water. The final volume is adjusted to 750 ml with deionized water. The gels are soaked in the ammoniacal silver nitrate solution for 10 min., then washed 3×5 min. with water. The developing solution contained 0.1 g of citric acid and 1 ml of formaldehyde/liter of deionized water. The gels are developed for 5 min. or 20 min. in this solution and placed in a solution containing 50 ml acetic acid/1 L water for 1 hour to stop the development. For storage purpose, the acetic acid solution is replaced by a glycerol:ethanol:water (2:10:88) solution.

Results and Discussion

The purpose of this study was to measure the effect of the catalyst system on silver staining in polyacrylamide gels polymerized with diacrylylpiperazine (PIP). It has been known for many years that catalyst systems have a major influence on the chemical and physical properties of the gels. Depending on the buffer used and the pH range chosen for the separation technique, different catalytic systems have been utilized. For the polymerization of multiple basic gels in a casting chamber, the use of TEMED and ammonium or potassium persulfate has been the most convenient and commonly employed catalyst system so far. However, this system has been shown to create a yellow background stain with silver (see FIG. 1). Both TEMED and persulfate produce this background despite extensive gel washes and pre-electrophoresis (FIG. 1). These findings suggest that those molecules are either bound to or entrapped into the gel or modify the polymer during polymerization. No other known alternative catalytic systems were suitable for the reasons outlined in the introduction.

A number of amine and diamine organic bases were tested as potential substitutes for TEMED. TEMED is an organic base with two tertiary amines separated by two carbons. The first compounds tested, triethylamine, 1,3-diaminopropane and dimethylaminoethylmorpholine, were poor catalytic agents. 3-dimethylaminopropylamine and 1-piperidinepropionitrile were better catalysts, but they produced an even darker background than TEMED. The presence of three carbons between the two amines or the addition of an oxygen seemed detrimental for a good polymerization. The dimethyl-ethylenediamine family gave the best catalytic system for the polymerization of the gels but they all produced almost the same yellow background as TEMED. From these results, it seemed that the best diamine compound should have at least a tertiary amine, if possible two, separated by two carbons. 1,4-dimethylpiperazine (DMPIP) is a diamine compound which contains two tertiary amine groups separated by two carbons. Indeed, it was found to be a good catalyst, not as potent as TEMED, but to give less background than TEMED with ammoniacal silver nitrate. Its structure is very similar to the crosslinker, diacrylylpiperazine, and not far at all from TEMED. In fact, if TEMED were cleaved in the middle of the ethylene group into two identical pieces, and if the resulting residues were inverted and rebonded, one would obtain DMPIP. In contrast, DMPIP gave more background than TEMED with dichromate silver stain.

The rapid polymerization of gel solution containing highly purified diacrylylpiperazine might be due partially to the catalytic effect of the crosslinker, itself. Diazabicyclo(2,2,2) octane did not give a good polymerization, probably because of its tertiary structure.

All the molecules tested produced a background staining, each with a different color: orange for 1,3-diaminopropane, yellow for the dimethylethylenediamine family, or brown for the propiontrile group. Despite the use of DMPIP, a yellow background stain still appears after prolonged silver staining.

Figure 2:
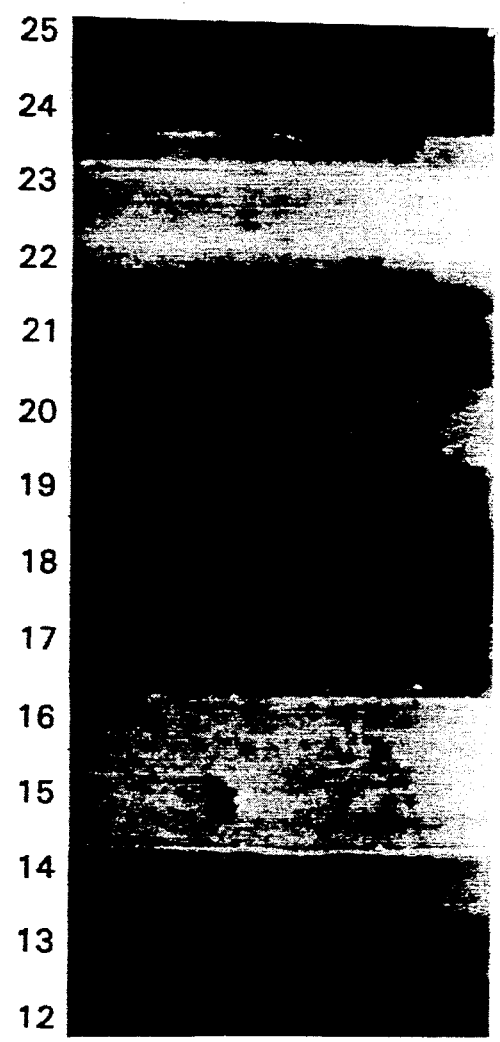
FIG. 2 is a photograph of an electrophoresis gel, which illustrates the effects of different "catalysts" and adjunct compounds on silver staining in polyacrylamide gels.

Since no further reductions in background staining could be achieved beyond that observed with DMPIP or TEMED, different salts were tested either to replace the organic bases and to be added to the persulfate or even to replace the persulfate. None of the salts tested (see FIG. 2) produced adequate polymerization if used alone. Only ammonium or potassium persulfate used with another compound produced good polymerization and their effect on the background staining was identical (FIG. 2, #14-17). However, the addition of different anions dramatically modified the background stain from a yellow stain for sulfate to a dark brown stain for permanganate. These results provide evidence that the molecules utilized in the catalytic system are bound within the gel matrix.

The addition of sodium sulfite accelerated the polymerization process, and gels were polymerized with APS and sulfite without organic base. However, sulfite increased the background staining more than TEMED or DMPIP. None of the other salts tested could replace the organic base. The addition of thiosulfate slowed down the polymerization, but it totally eliminated the appearance of any background during prolonged development times with cooled developer solution, despite the use of persulfate and TEMED or DMPIP (FIG. 2, #21). Polymerization of slab gels, utilized in the second dimension of 2-dimensional gel electrophoresis, with DMPIP or TEMED, persulfate and thiosulfate, resulted in separation of proteins with no modification of the apparent relative molecular mass. The two-dimensional gel electrophoresis picture of a plasma sample showed an increased number of spots (5%) secondary to the prolonged development time without any apparent background.

FIG. 1: Effects of different diamine catalysts on silver staining in polyacrylamide gels.

| Compound name | Volume (μL) |
| --- | --- |
| 1. N,N,N'N'-tetramethylethylenediamine (TEMED) | 20 |
| 2. 1,3-diaminopropane | 150 |
| 3. 3-dimethylaminopropylamine | 100 |
| 4. 1-piperidinepropionitrile | 50 |
| 5. N,N-dimethyl-ethylenediamine | 10 |
| 6. N,N-dimethyl-N'-ethyl-ethylenediamine | 10 |
| 7. N,N,N'N'-tetramethyl-ethylenediamine (TEMED) | 10 |
| 8. 1,4-dimethylpiperazine (DMPIP) | 60 |
| 9. 4-[2-(dimethylamino)ethyl]morpholine | 400 |
| 10. 1,4-diazabicyclo(2,2,2)octane (DABCO) | 800 |
| 11. 1,4-dimethylpiperazine (DMPIP) | 60 |

(Numbers 1 to 11 correspond to Lanes 1 to 11, respectively.)

(Numbers 1 to 11 correspond to Lanes 1 to 11, respectively.)

A volume of 150 μL of ammonium persulfate solution is used in all gel bands, except for the band containing 1,4-diazabicyclo(2,2,2)octane, which required 800 μL of ammonium persulfate solution for an identical polymerization rate. The varying amounts of diamines are chosen to obtain similar rates of polymerization. It is impossible to get a gel with equivalent mechanical properties with triethylamine, 1,3-diaminopropane or 1,5-diazabicyclo(4,3,0)non-5ene. The polymerization is much poorer with these reagents. All the bands are polymerized with diacrylypiperazine (PIP) as the crosslinking agent, except band one, which is polymerized with methylenebisacrylamide (BIS) and TEMED to illustrate the currently commonly employed gel polymerization system.

FIG. 2: Effects of different catalysts and adjunct compounds on silver staining in polyacrylamide gels.

| Diamine | Compound(s) name | Crosslinker |
| --- | --- | --- |
| 12. TEMED | Ammonium persulfate (APS) | BIS |
| 13. TEMED | APS | PIP |
| 14. TEMED | Potassium persulfate (KPS) | PIP |
| 15. DMPIP | KPS | PIP |
| 16. DMPIP | APS | PIP |
| 17. TEMED | KPS + Sodium sulfate | PIP |
| 18. TEMED | KPS + Sodium permanganate | PIP |
| 19. TEMED | KPS + Sodium bisulfite | PIP |
| 20. TEMED | KPS + Sodium hydrosulfite | PIP |
| 21. TEMED | KPS + Potassium metabisulfite | PIP |
| 22. TEMED | KPS + Magnesium sulfate | PIP |
| 23. TEMED | KPS + Sodium Thiosulfate | PIP |
| 24. TEMED | KPS | PIP |
| 25. 0 | KPS (6 g/L) | PIP |

(Numbers 12 to 25 correspond to Lanes 12 to 25, respectively.)
APS: 1 g/L
KPS: 0.67 g/L
All other salt solutions: 0.75 g/L
TEMED (N,N,N'N'-tetramethylethylenediamine): 3.3 mL/L
DMPIP (dimethylpiperazine): 20 mL/L
BIS: methylene-bisacrylamide 0.8 g/100 mL stock solution
PIP: diacrylyl-piperazine 0.1 g/100 mL stock solution
0: no diamine used the concentration of persulfate is increased.

This gel demonstrated that the lowest background staining could be achieved by polymerizing a polyacrylamide gel with diacrylylpiperazine (PIP) as crosslinking agent, with dimethylpiperazine and ammonium or potassium persulfate as the catalytic system. Background staining is further minimized if the catalytic system contains sodium thiosulfate.

Despite extensive washing procedures and/or pre-electrophoresis of the gel, the background staining is profoundly affected by the diamine, the salts and the oxido-reducing catalyst. This observation provides indirect evidence that these compounds may be incorporated into the structure of the gel. Small ions should have been removed by pre-electrophoresis and washing procedures. The diamine bases and the anions are probably incorporated into the gel matrix. The lack of an effect with the cations suggest that they are not incorporated into the gel under the basic conditions utilized in these experiments In conclusion, it was previously determined that the use of crosslinking agents without amide groups or with amide groups, that are substituted twice, such as diacrylylpiperazine, prevented the rapid appearance of a background stain and reduced the total background after prolonged staining with ammoniacal silver. The addition of thiosulfate in "SDS" slab gels to DMPIP or TEMED and APS totally prevents the appearance of background staining with ammoniacal silver nitrate during a prolonged development time and profoundly reduces the appearance of background staining with dichromate silver staining. This catalytic system enhances silver stain protein spot definition.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed:

1. A method for preparing a polyacrylamide gel comprising polymerizing acrylamide with diacrylylpiperazine in the presence of a catalyst system which comprises dimethylpiperazine in combination with ammonium persulfate or potassium persulfate.

2. The method according to claim 1, wherein said catalyst system further comprises sodium thiosulfate.

3. The method according to claim 2, wherein said acrylamide and said diacrylylpiperazine are present in a weight ratio of about 15 to 0.4.

4. The method according to claim 2, wherein said acrylamide and said diacrylylpiperazine are present in an amount of about 13 g and about 0.4 g, respectively, per 100 ml of water.

5. The method according to claim 2, wherein said catalyst system is present in an amount from about 0.8 mg to about 16 mg per gram of the total weight of said acrylamide and said diacrylylpiperazine.

6. The polyacryalmide gel produced by the method according to claim 1.

7. The polyacrylamide gel produced by the method according to claim 2.

8. The polyacrylamide gel produced by the method according to claim 3.

9. The polyacrylamide gel produced by the method according to claim 4.

10. The polyacrylmide gel produced by the method according to claim 5.

11. An improved silver stain method utilizing a polyacrylamide gel for the detection of biomaterials with reduced background staining, wherein the improvement comprises the use of a polyacrylamide gel comprising a matrix of arylamide with diacrylylpiperazine polymerized in the presence of a catalyst system which comprises dimethylpiperazine in combination with ammonium persulfate or potassium persulfate.

12. The method according to claim 11, wherein said catalyst system further comprises sodium thiosulfate.

13. The method according to claim 12, wherein said acrylamide and said diacrylylpiperazine are present in a weight ratio of about 15 to 0.4.

14. The method according to claim 12, wherein said acrylamide and said diacrylylpiperazine are present in an amount of about 13 g and about 0.4 g, respectively, per 100 ml of water.

15. The method according to claim 12, wherein said catalyst system is present in an amount from about 0.8 mg to about 16 mg per gram of the total weight of said acrylamide and said diacrylylpiperazine.

* * * * *